United States Patent [19]
Knoepfler

[11] Patent Number: 5,282,796
[45] Date of Patent: Feb. 1, 1994

[54] SCOPIC PROBE

[76] Inventor: Dennis J. Knoepfler, 1383 Whitaker La., Amelia, Ohio 45102

[21] Appl. No.: 904,386

[22] Filed: Jun. 25, 1992

Related U.S. Application Data

[63] Continuation-in-part of Ser. No. 641,010, Jan. 14, 1991, abandoned.

[51] Int. Cl.$^5$ .............................................. A61B 17/32
[52] U.S. Cl. .................................. 606/1; 606/106; 604/264
[58] Field of Search ................ 606/106, 107–138, 606/1, 161, 222–227; 433/156, 15, 20; 604/281, 264, 158, 164

[56] References Cited

U.S. PATENT DOCUMENTS

| | | | |
|---|---|---|---|
| 667,726 | 2/1901 | McDade | 606/160 |
| 1,708,578 | 4/1929 | Hyde | 606/107 |
| 2,117,312 | 5/1938 | Gauly | 606/107 |
| 4,441,485 | 4/1984 | Reynolds | 606/106 |
| 4,572,180 | 2/1986 | Deenadayalu | 606/106 |
| 4,683,885 | 8/1987 | Hutter et al. | 606/222 |
| 4,950,272 | 8/1990 | Smirmaul | 606/107 |
| 4,991,777 | 2/1991 | Sato | 604/275 X |
| 5,074,867 | 12/1991 | Wilk | 604/264 X |

FOREIGN PATENT DOCUMENTS

| | | | |
|---|---|---|---|
| 629923 | 10/1978 | U.S.S.R. | 606/106 |
| 1266536 | 7/1984 | U.S.S.R. | 606/106 |

Primary Examiner—Peter A. Aschenbrenner
Attorney, Agent, or Firm—Wood, Herron & Evans

[57] ABSTRACT

A scopic probe adapted to dissect various tissue includes a shaft and a wire tip. The wire tip includes an arcuate portion that is at a 90° angle relative to the shaft. The arcuate or loop portion then extends to a linear tip that is parallel to the shaft. The tip is used to separate tissue which in turn is hooked by the loop allowing the surgeon to visualize depth and divide the hooked tissue. This permits a surgeon to perform tasks generally requiring several instruments with only one instrument.

9 Claims, 2 Drawing Sheets

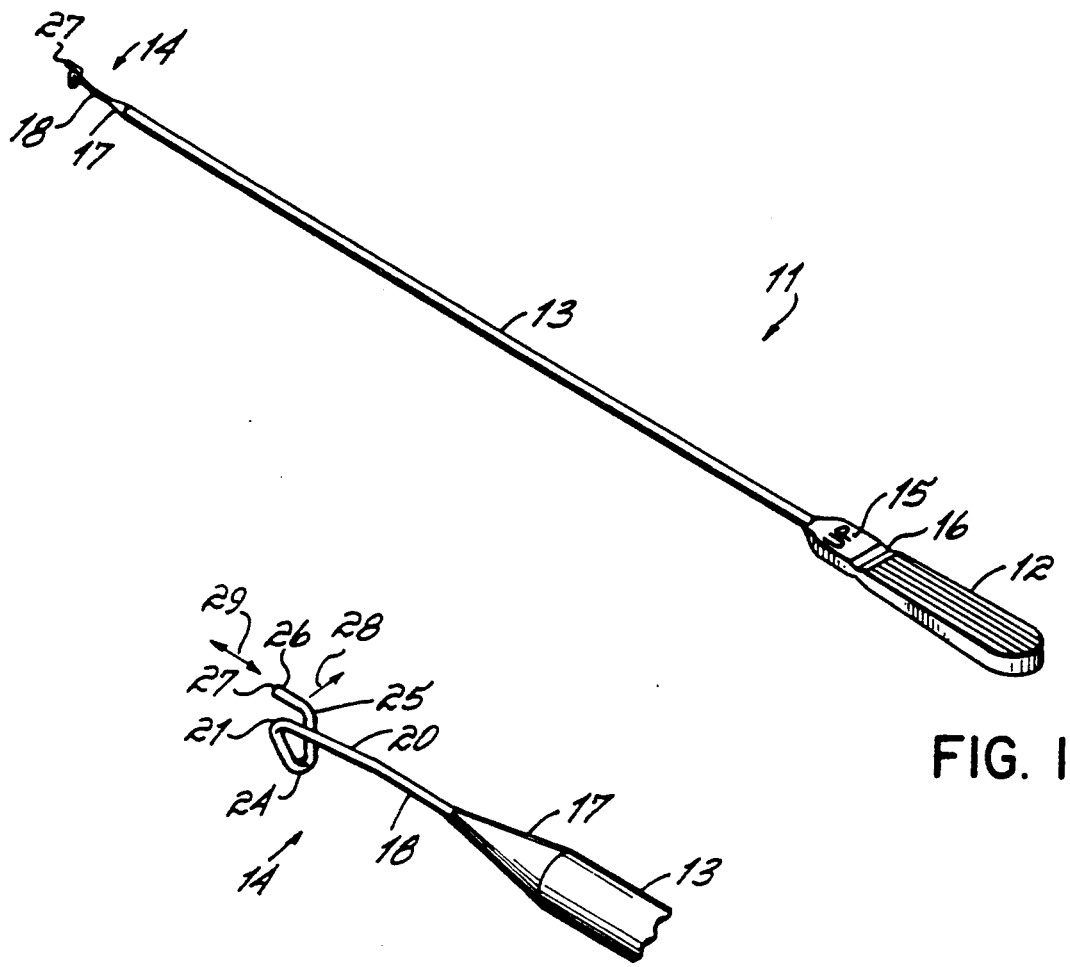
FIG. 1
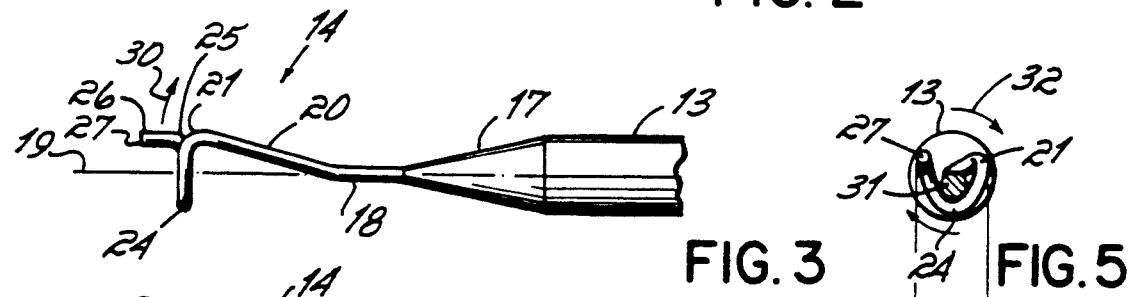
FIG. 2
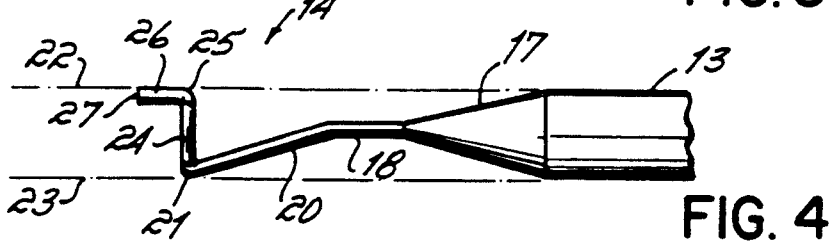
FIG. 3
FIG. 5
FIG. 4
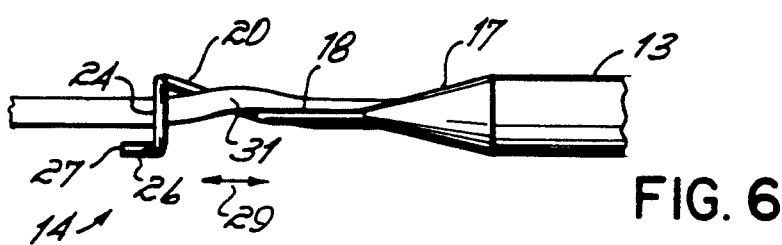
FIG. 6

SCOPIC PROBE

RELATED APPLICATIONS

This application is a continuation-in-part of application Ser. No. 07/641,010, filed Jan. 14, 1991, now abandoned.

BACKGROUND OF THE INVENTION

In surgical procedures, it is frequently necessary to dissect out ducts, veins, nerves and other sinuous tissue from associated tissue. Particular examples of this are: isolating the cystic duct and cystic artery prior to clipping and dividing these; dissecting out the Vagus nerve or its branches when performing Vagotomies for ulver surgery; dissecting mesenteric vessels for future large and small bowel resections; and dissecting hilar vessels for pulmonary resectioning; and dissecting out vessels for doing hysterectomies or nephrectomies.

In typical procedures, this does not present a problem. By using a combination of scalpel, forceps and probes, a surgeon can separate and pull apart the desired vein or duct and separate this from the associated tissue. The surgeon has two free hands and an open area to work with to accomplish this.

In scopic and laparascopic procedures, this is not the case. To begin with, only a limited number of instruments can be used at one time, generally only one or two. Further, the instruments, due to the way they are inserted into the body cavity, have a limited range of motion. For this reason, it is very difficult to separate veins, ducts and the like from the associated tissue. It can be done, but it generally requires substantial effort and time. When scalpels are employed, the possibility of cutting thevein or duct which is being separated is increased.

SUMMARY OF THE INVENTION

Accordingly, it is an object of the present invention to provide a probe to dissect tissue in laparascopic procedures and other scopic surgeries.

Further, it is an object of the present invention to provide such a probe to separate veins, ducts, and other sinuous tissue from its associated tissue. And more particularly, it is an object to provide a single instrument to dissect such tissue during a laparascopic procedure. It is also an object of the present invention to provide a scope probe which permits the surgeon to suspend the isolated structure from the surrounding tissue in the tip of the device, allowing the surgeon to visualize and easily clip and divide the structure.

The objects and advantages of the present invention will be further appreciated in light of the following detailed description and drawings in which:

BRIEF DESCRIPTION OF THE DRAWINGS

FIG. 1 is a perspective view of the present invention;

FIG. 2 is an enlarged view of the present invention partially broken away;

FIG. 3 is a side plan view of the apparatus as shown in FIG. 2;

FIG. 4 is an overhead plan view of the apparatus as shown in FIG. 2;

FIG. 5 is a front plan view taken at lines 5—5 of FIG. 2;

FIG. 6 is an overhead plan view of the apparatus of the present invention in use;

DETAILED DESCRIPTION

Figure 7:
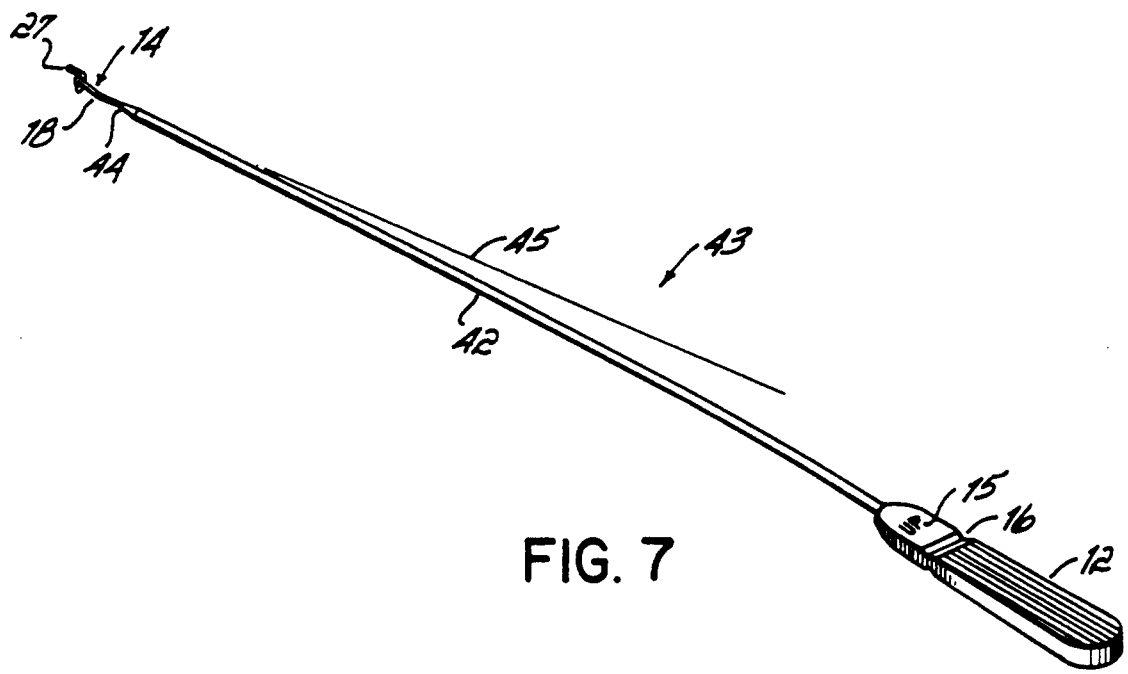
FIG. 7 is a perspective view of an alternate embodiment of the present invention.

As shown in FIG. 1, the present invention is a probe or nerve hook 11 which includes a handle 12, shaft 13 and tip portion 14. The entire probe is preferably formed from suitable material such as stainless steel.

The handle which can be of any generally acceptable shape, includes indicia 15 to indicate the top of the probe 11. The handle 12 which is generally a spoon-type handle includes a thumb channel 16 to allow the thumb to guide the instrument and when the handle is being grasped by a surgeon's hand.

The shaft 13 is of a length which makes it suitable for laparascopic procedures. Of course the intended laparascopic procedure will determine the exact length, but generally such procedures require a shaft length of at least about 30-35 cms. At the end of the shaft 13 opposite the handle 12 is a tapered portion 17. Extended from the tapered portion 17 is wire tip 18. Wire tip 18 is relatively rigid which prevents it from bending during use. To dissect tissue, the wire should have a diameter of 1/32" (0.03125") to about ⅛" (0.125").

As particularly shown in the FIGS., the wire tip 18 extends out at the central axis 19 of shaft 15. The wire tip 18 includes an angled portion 20 which extends to a bend 21. Bend 21 is a right angle bend.

Figure 9:
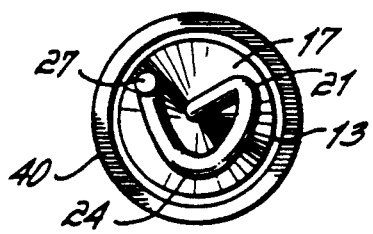
FIG. 9 is a front plan view taken from FIG. 8 depicting the present invention in use.

It is noted that the entire wire tip 18 remains within the diameter of shaft 13 (FIG. 4). The outer edges of the diameter of shaft 13 are shown by lines 22 and 23. As shown by FIG. 9, the maximum diameter of tip 18 is the internal diameter of the cannula 40 through which it extends. Generally, cannulas are 5 to 10 millimeters wide (never more than 15 millimeters wide) for laparascopic procedures. Accordingly, the tip should be less than 15 millimeters in diameter and less than 5 or 10 millimeters depending on the cannula.

As shown in FIG. 5, the diameter of the tip is the widest side to side dimension as shown by double pointed arrow 18a. Bend 21 lies approximately at line 23. The wire tip 18 extends from bend 21 through an arcuate portion 24. The plane of arcuate portion 24 is not parallel to the axis 19 and as shown roughly perpendicular to the axis 19 of shaft 13 (FIG. 4). The angle between this plane of arcuate section 24 and axis 19 should be greater than 0° (in line with the axis) and preferably at last 15° up to 90°. The arcuate portion 24 is basically a 180° arcuate portion although a smaller arc could be utilized in the present invention. Generally, however, the arc should exceed 90° and be less than 360°. The arcuate portion 24 ends at bend 25 which likewise lies at about line 22 so that the entire wire tip portion 14 remains within the diameter of shaft 13. This then concludes with a straight portion 26 which extends from bend 25 parallel to axis 19 and roughly at line 22. The linear portion then ends with a point 27.

This device is particularly suitable for use in dissecting the cystic bile duct or Vagus nerves. The handle of the device 12 is grasped by the surgeon's hand. The indicia 15 indicating which portion of the instrument is up is significant since it also would indicate that the linear portion 26 lies to the righthand side of the instrument so the surgeon will always know where this linear portion 26 lies. A mirror image of this instrument could also be made with the linear portion 26 lying to the left portion. The indicia 15 allows the surgeon to know on which side this linear portion 26 lies.

Figure 8:
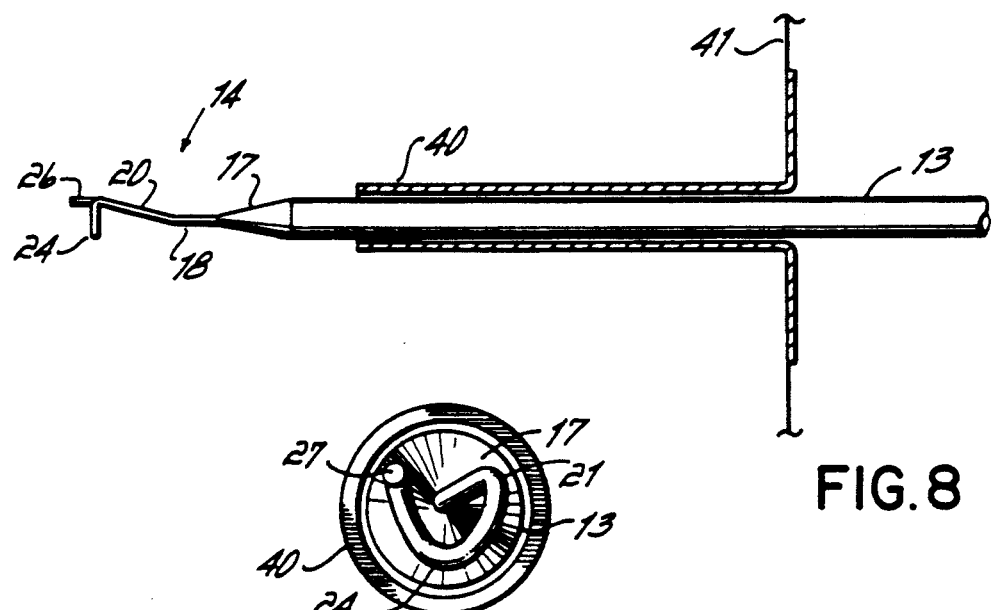
FIG. 8 is a side plan view partially in cross-section of the present invention in use.

As shown in FIG. 8, the instrument 11 would be inserted through a cannula 40 into the body 41. As shown, tip 18 easily fits through the cannula. The linear portion 26 of the device first contacts tissue. This is pressed against tissue as indicated by arrow 28. This is then moved backwards and forwards as shown by arrow 29 (FIG. 2). By the combined forces, as shown by arrows 28 and 29, the linear portion 26 will work its way into tissue in the direction of arrow 28. Once being worked into tissue, the device can be tilted slightly so that point 27 starts to dig into the tissue. The top portion 26 will then be worked upwardly in the direction of arrow 30. This should basically put the tip portion 18 in the position shown in FIG. 5 relatively to a vein 31. Once this is accomplished, the device can be rotated in the direction shown by arrow 32 and the reciprocating motion indicated by arrow 29 can be resumed to successfully separate the duct from the associated tissue as shown in FIG. 6.

The advantage of this is that it can all be accomplished with one hand. The instrument used is simply a probe and is not pointed, therefore, rupturing the duct is unlikely. It can be done quickly because the use of only one apparatus eliminates the need to remove one apparatus and insert another into the body cavity. The size of the tip provides an effective instrument which can be inserted in cannula for laparascopic procedures. Thus, the present invention is inexpensive, effective and saves time.

FIG. 7 shows a slightly modified version of the present invention. In this embodiment, the shaft 42 of the probe 43 is curved very slightly, about 3°-5° over the length of the shaft (30-35 cm). This facilitates control of the instrument during use. The curvature is so slight, however, it still enables the shaft to easily fit through a canula which has a length of approximately 3-5 inches. In this embodiment, the axis of the shaft would be considered the tangent to the shaft at the tip portion 44 shown as a dotted line 45. But in any event, this slight curvature provides for better control of the instrument during use.

This has been a description of the present invention along with the best mode of practicing the invention currently known.

However, the invention should only be defined by the appended claims wherein I claim:

1. In combination a dissecting probe for a scopic procedure and a laparoscopic cannula having an internal diameter, said probe extended through said cannula
   said probe having a center shaft having an axis;
   a wire tip extended from said shaft;
   said wire tip having an arcuate portion having a plane which is not parallel to said axis wherein said first end of said arcuate portion is connected to said shaft and a second end of said arcuate portion is attached to a dissecting linear wire portion pointed away from said arcuate portion and said shaft wherein said wire tip has a diameter less than the internal diameter of said cannula.

2. The combination claimed in claim 1 wherein the plane of said arcuate portion is at an angle relative to said axis of 15° to 90°.

3. The combination claimed in claim 1 wherein said shaft has a diameter and wherein said tip has a diameter no greater than 10 millimeters whereby said tip can easily fit through said laparascopic cannula.

4. The combination claimed in claim 1 wherein said arcuate portion extends from about 90° to less than about 360°.

5. The combination claimed in claim 4 wherein said probe includes a handle and said handle includes indicia indicating the relative location of linear the portion of the tip.

6. A dissecting probe for a scopic procedure comprising:
   a handle;
   a center shaft extended from said handle said shaft having a diameter;
   a wire tip extended from said shaft;
   said tip having an arcuate portion forming a 90° to less than 360° loop said arcuate portion having a plane at a right angle to said axis;
   a first end of said arcuate portion connected to said shaft and a second end of said arcuate portion extending to a linear portion which extends parallel with said axis; and
   said tip having a diameter no greater than the diameter of said shaft.

7. The probe claimed in claim 1 wherein said tip has a diameter less than 15 millimeters.

8. The combination of a laparascopic cannula and a dissecting probe,
   said cannula having an internal diameter;
   said probe extended through said cannula and comprising:
   a center shaft having an axis, and a wire bent to form a wire tip at one end and a handle portion at a second end of said shaft wherein said wire tip has an arcuate portion having a plane which is not parallel to said axis wherein said first end of said arcuate portion is connected to said shaft and a second end of said arcuate portion is attached to a dissecting linear wire portion parallel with said axis;
   wherein said tip has a diameter no greater than the internal diameter of said cannula.

9. The combination claimed in claim 7 wherein said wire has a diameter no greater than 0.125".

* * * * *